Figure 1:
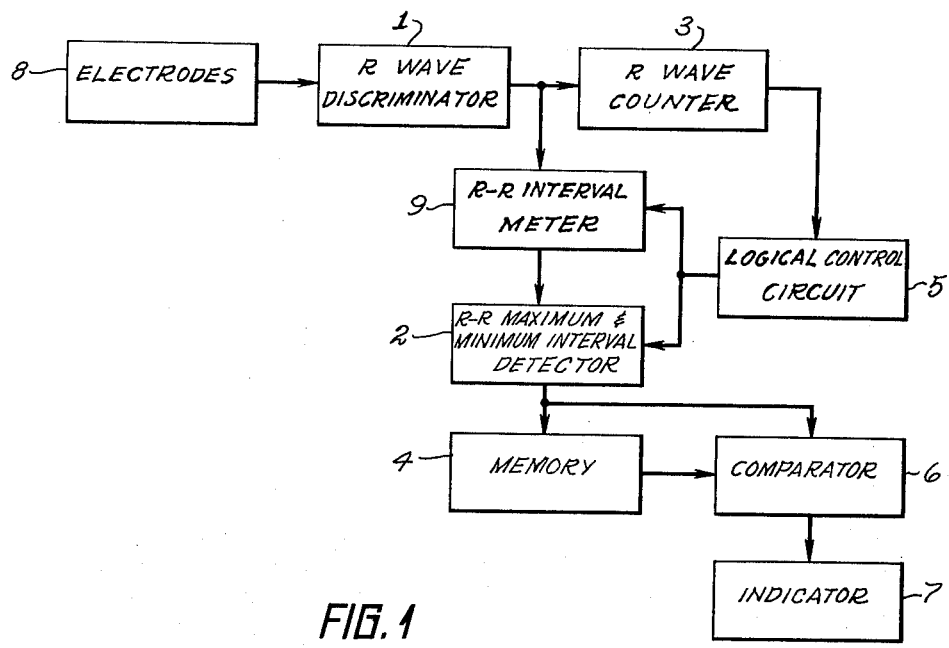

United States Patent [19]

Bolshov et al.

[11] 3,946,725

[45] Mar. 30, 1976

[54] METHOD FOR CONTROLLING THE LEVEL OF ANAESTHESIA IN SURGERY AND APPARATUS FOR EFFECTING SAME

[76] Inventors: Vladimir Mikhailovich Bolshov, ulitsa akademika Pavlova, 5/2, kv. 44, Moscow; Vyacheslav Evgenievich Voinor, Kirovogradskaya ulitsa, 42, Korpus 1, kv. 500, Moscow; Solomon Zalmanovich Kletskin, Moskovskaya oblast, ulitsa Karpovskaya, 45/2, kv. 12, Pavlovsky Posad; Viktor Julievich Ostrovsky, Proletarsky prospekt, 7, kv. 76, Moscow; Valery Vladimirovich Soloviev, ulitsa Oleko Dundicha, 29, kv. 39, Moscow; Nina Yakovlevna Ter-Kasparova, Moskovskoi oblasti, Moskovskoe shosse, 41, kv. 76, Dolgoprudny, all of U.S.S.R.

[22] Filed: Mar. 26, 1974

[21] Appl. No.: 454,797

[52] U.S. Cl. .............................................. 128/2.06 R
[51] Int. Cl.² .............................................. A61B 5/04
[58] Field of Search .......... 128/1 C, 2.06 A, 2.06 F, 128/2.06 R, 2.1 B

[56] References Cited
UNITED STATES PATENTS

| | | | |
|---|---|---|---|
| 3,513,834 | 5/1970 | Suzuki et al. | 128/2.1 B |
| 3,518,983 | 7/1970 | Jorgenson | 128/2.06 A |
| 3,524,442 | 8/1970 | Horth | 128/2.06 A |
| 3,820,025 | 6/1974 | Lahr et al. | 128/2.06 A |

FOREIGN PATENTS OR APPLICATIONS

| | | | |
|---|---|---|---|
| 806,703 | 6/1951 | Germany | 128/2.1 B |
| 251,937 | 2/1970 | U.S.S.R. | 128/2.06 A |

*Primary Examiner*—William E. Kamm
*Attorney, Agent, or Firm*—Robert E. Burns, Emmanuel J. Lobato, Bruce L. Adams

[57] ABSTRACT

The method consists in that immediately prior to surgery the difference between the maximum and minimum lengths of the R—R intervals for a predetermined number of heart contractions of the patient to be operated on is measured, this measured difference being accepted as a standard. Then, in the course of operation, the current values of difference between the maximum and minimum lengths of the R—R intervals for the same predetermined number of heart contractions are measured. Deviations of the measured current values of difference from the initial or reference value of difference between the maximum and minimum lengths of the R—R intervals characterize the degree of incompetence of anaesthesia and the level of anaesthesia. The means realizes the method by processing the data furnished by ECG electrodes applied to the body of the patient undergoing surgery.

4 Claims, 2 Drawing Figures

U.S. Patent   March 30, 1976   3,946,725

METHOD FOR CONTROLLING THE LEVEL OF ANAESTHESIA IN SURGERY AND APPARATUS FOR EFFECTING SAME

The present invention relates to the field of medical anaesthesiology and, more particularly, to a method for controlling the level of anaesthesia in surgery by measuring the biocurrents of the organism subjected to anaesthesia. The invention also relates to means realizing said method and adapted, inter alia, to check the state of the subject in the course of surgery with a view to determining the competence of the premedication level.

Several methods for determining the level or degree of anaesthesia are known to those skilled in the art. Among these, the most wide-spread by far is the technique of determining the level of anaesthesia by the degree of inhibition of cerebral bioelectrical activity, described by S. N. Yefuni in "Electroentsefalografiya v klinicheskoi anesteziologii" /Electroencephalography in Clinical Anaesthesiology/, MEDGIZ Publishers, 1961.

According to this known method, the level of anaesthesia is determined by measuring the degree of inhibition of electrical activity of the nervous centers of the body.

The known method has several disadvantages, such as the discrepancy between the degree of inhibition of electrical activity of the nervous centers and the degree of anaesthesia in response to drugs and reflex effects, as well as different pathological states of the patient.

Also known are means for determining the level of anaesthesia, such as, for instance, a "Detector of Anaesthesia Stages" comprising a signal processing unit and a display unit, which is being commercially produced in the USSR. The disadvantage of this means consists in that the signal processing unit thereof comprises a cerebral biopotential amplifier, a frequency filter, a detector and a pointer indicator coupled thereto. Such an arrangement is inadequate for providing objective information as to the degree of anaesthesia in different forms of surgical intervention.

It is an object of the present invention, therefore, to obviate the above-mentioned disadvantages and to provide an objective anaesthesia-level monitoring method for determining the competence of anaesthesia in surgery at a higher level of accuracy, as well as means using said method which would be simple in design and trouble-free in operation.

It is another object of the present invention to provide an anaesthesia-level controlling method which would ensure objective and accurate indication of the competence of anaesthetization of the patient being operated on.

It is still another object of the present invention to provide an anaesthesia-level monitoring method which would provide for actively correcting the incompetence of premedication and maintaining a predetermined level of anaesthesia.

It is yet another object of the present invention to provide a trouble-free and simple means to effect the proposed method for determining the competence of anaesthesia.

The invention contemplates providing a method and means for monitoring the level of anaesthesia on the basis of such a parameter of the body which would most objectively and adequately indicate the level and competence of premedication.

These and other objects are attained by the provision of a method for monitoring the level of anaesthesia in surgery by measuring the biocurrents of the patient being operated on, characterized in that immediately prior to the operation the maximum and minimum lengths of the R—R intervals of heart contractions of the patient are measured in order to determine the difference between the maximum and minimum R—R intervals for a predetermined number of heart contractions, after which in the course of surgery, the values of the difference between the maximum and minimum R—R interval lengths for the same predetermined number of heart contractions are determined, and, by comparing said measured current values with the initially found value of difference of the R—R intervals taken as a reference value, the level of anaesthesia is determined.

Such a technique of monitoring the state of the patient gives the most objective and accurate evaluation of the level of anaesthesia in surgery and of the competence of anaesthesia.

In one embodiment of the invention, said initially measured difference of the R—R intervals is taken as an optimum for a given organism subjected to anaesthesia, so that in the course of operation the task is to maintain the current value of difference of the R—R intervals at a level close to or equalling said optimum level.

By maintaining the current value of the R—R interval difference at a desired level it is possible to maintain a sufficient level of anaesthesia in the course of surgery.

In accordance with the present invention, an apparatus for controlling the level of anaesthesia embodying said method is characterized in that it comprises ECG electrodes applied to the body of the patient to record heart biopotentials, a discriminator isolating R-waves from said signal, a R-wave counter coupled at the output of the discriminator and preset to a predetermined number of heart contractions, a R—R interval length meter coupled at the output of the R-wave discriminator, said counter being coupled to said meter so as to disconnect the R—R interval length meter as soon as the number of heart contractions to which the R-wave counter has been preset is over, and a detector of the maximum and minimum R—R intervals coupled at the output of said meter to determine the difference between the extreme values of R—R intervals.

The foregoing apparatus is one of the possible versions of a device embodying the above-mentioned method; in spite of its fairly simple design, it provides for reliable monitoring of the level of anaesthesia of the body subjected to surgery.

Finally, in accordance with the present invention, there is provided a logical control circuit which is coupled at the output of the R-wave counter and connected to said R—R interval length meter and to said detector in order to provide for said disconnection of the R—R interval length meter and to furnish a signal actuating the detector to determine the difference between the extreme values of R—R intervals, whereas at the output of the detector there is provided a memory unit which stores the value of R—R interval difference as measured prior to surgery, and between the memory unit and the logical control circuit there is coupled a comparator which compares the R—R interval difference value stored in the memory unit with the current values of said difference measured in the course of surgery.

Figure 2:
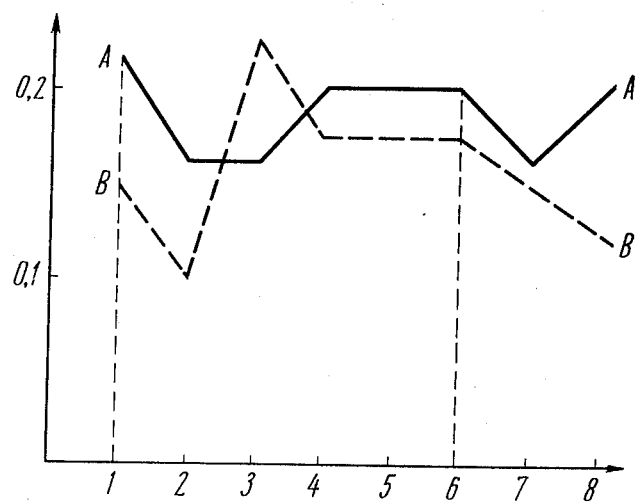

Presented hereinbelow is a detailed description of an exemplary embodiment of the present invention taken in conjunction with the accompanying drawings, wherein:

FIG. 1 is a block diagram of an apparatus for monitoring the level of anaesthesia, in accordance with the present invention; and FIG. 2 is a graph illustrating the process of monitoring the level of anaesthesia, wherein the values of difference of the extreme R—R intervals given in seconds are plotted on the ordinate, while plotted on the abscissa are the stages of the operation designated by numerals, in accordance with the accompanying table.

The proposed monitoring method is realized by that, prior to anesthetization, the difference between the maximum and minimum R—R intervals for a predetermined number of cardiac cycles or heart contractions is calculated, this difference being taken as a standard, after which, throught the operation, the values of difference between the maximum and minimum R—R interval lengths for the same number of cardiac cycles are measured, the reference value is compared with the values obtained in the course of surgery, and the level of anaesthesia is evaluated by the degree of deviation of these differences from the standard.

The proposed method for determining the level of anaesthesia is illustrated by a table of data and a graph of the table data. The table gives the values of difference $\Delta R—R$ between the maximum and minimum R—R interval lengths in seconds for two patients which were calculated during surgery.

Table

| Stage of operation | No. of stage | $\Delta R$–R Sec Patient A | $\Delta R$–R Sec Patient B |
|---|---|---|---|
| 1 | 2 | 3 | 4 |
| Type of basic anaesthesia | 1 | 0.21 | 0.15 |
| Operation | 2 | 0.16 | 0.1 |
| | 3 | 0.16 | 0.225 |
| | 4 | 0.2 | 0.175 |
| | 5 | 0.2 | 0.175 |
| Termination of operation | 6 | 0.2 | 0.175 |
| Postoperative period | 7 | 0.16 | 0.15 |
| | 8 | 0.2 | 0.125 |

Referring to the graph, plotted on the ordinate are the values $\Delta R$—R in seconds, and the abscissa indicates the stages of surgery given numerical designations.

EXAMPLE 1

The initial difference between the maximum and minimum R—R intervals of surgical patient A for a predetermined number of cardiac cycles measured at the instant when basic anaesthesia was administered, equalled 0.21 sec. In the course of operation, the values of the difference between the maximum and minimum R—R intervals for the same number of cardiac cycles were measured and compared with the initial value. As is seen from the graph of FIG. 2, during the operation the values of difference between the extreme R—R intervals of patient A never exceeded the initial one. Parallel biochemical analysis revealed the competence of anaesthesia.

EXAMPLE 2

The initial difference between the maximum and minimum R—R intervals of surgical patient B for a predetermined number of cardiac cycles measured at the moment when gasic anaesthesia was administered, amounted to 0.15 sec. In the course of operation, the values of difference between the maximum and minimum R—R intervals for the same number of cardiac cycles were measured and compared with the initial value. As is seen from the graph of FIG. 2, the values of difference between the extreme R—R intervals of Patient B during the operation exceeded the initial value. Parallel biochemical analysis revealed the incompetence of anaesthesia.

The proposed method is an objective and accurate way of determining the level of anaesthesia.

The essential features of the proposed apparatus effecting the method of the invention are illustrated by a drawing which is a block diagram of the apparatus for determining the level of anaesthesia. The apparatus of this invention comprises an R-wave discriminator 1, a detector 2 which determines the difference between the maximum and minimum lengths of the R—R intervals, an R—R interval counter 3, a memory unit 4, a logical control circuit 5, a comparator 6 and a display unit 7, electrodes 8 and an R—R interval length meter 9.

The apparatus of this invention operates in the following manner.

Cardiosignals from electrodes 8 recording the biopotentials of the heart are supplied to the input of the R-wave discriminator 1. The R-waves isolated by the discriminator 1 are supplied, by way of an R—R interval length meter 9, to the input of the detector 2 for determining the difference between the maximum and minimum R—R intervals measured by the meter 9 and to the input of the R-wave counter 3. The counter 3 counts the number of R—R intervals, and as soon as a predetermined number or array of sequential cardiac cycles have arrived, the counter 3 furnishes a signal to the input of the logical control circuit 5.

The discriminator isolated R-waves are fed to the input of the detector 2 which measures the difference between the maximum and minimum lengths of the R—R intervals. After the last R-wave has been processed, the measured value of difference is sent by the logical control circuit 5 to the memory unit 4 for storage, whereupon the logical control circuit 5 sends a resetting signal to the R—R interval counter 3 and to the detector 2 measuring the difference between the maximum and minimum lengths of the R—R intervals so that the next value of difference may be similarly calculated.

Having received the above-mentioned values by the above-described technique, the logical control circuit 5 sends a signal to the comparator 6 to compare the newly calculated value with the one stored in the memory unit 4. Should there be any deviation of the current value of the difference from the standard, the circuit 6 sends a signal to the display unit 7 which registers the degree of deviation indicative of the level of anaesthesia.

In a specific embodiment of the apparatus of this invention described hereinabove, a D.C. amplifier combined with a frequency filter may be employed as the R-wave discriminator 1, a coincidence circuit as the detector 2 determining the difference of the extreme values of R—R intervals, and an electronic decade counter as the R-wave counter 3. Said R—R interval length meter 9 may be a shift register combined with a flip-flop, the memory unit 4 may be a trigger counter, the comparator 6 may be a coincidence circuit with a shift register, and the logical control circuit 5 may be interconnected AND, OR and NOT circuits and a trigger. The way the proposed means for monitoring the level of anaesthesia can be practically constructed will be apparent to those skilled in the art, for which reason the foregoing specification omits non-essential technical features which may be chosen depending on the requirements and conditions of measurement.

Many modifications will occur to those skilled in the art which clearly fall within the true spirit and scope of this invention as set forth in the following claims.

What is claimed is:

1. A method for providing an optimum level of anaesthesia during surgery comprising:
   measuring immediately prior to surgery the maximum interval and the minimum interval between consecutive R waves which occur during a predetermined number of heart contractions of an anaesthetized patient on which surgery is to be performed;
   calculating the difference between the maximum interval and the minimum interval between consecutive R waves which occurred immediately prior to surgery;
   measuring during the course of surgery the maximum interval and the minimum interval between consecutive R waves which occur during said predetermined number of heart contractions;
   calculating the difference between the maximum interval and the minimum interval between consecutive R waves which occurred during the course of surgery;
   comparing the difference between the maximum and minimum intervals between consecutive R waves which occurred during surgery with the difference between the maximum and minimum intervals between consecutive R waves which occurred immediately prior to surgery; and
   administering anaesthetic to the patient to minimize a difference between the difference between the maximum interval and minimum interval between consecutive R waves which occurred during surgery and the difference between the maximum interval and minimum interval between consecutive R waves which occurred immediately prior to surgery.

2. A method for providing an optimum level of anaesthesia during surgery comprising:
   sensing biopotentials including R waves of the heart of an anaesthetized patient on which surgery is to be performed;
   discriminating the R waves from the sensed biopotentials;
   measuring, immediately prior to surgery, the intervals between successive ones of the R waves;
   detecting the difference between the maximum interval and the minimum interval between successive ones of the R waves occurring prior to surgery;
   simultaneously with measuring the intervals and detecting the difference between the maximum interval and the minimum interval, counting the successive R waves and terminating measuring the intervals and detecting the difference between the maximum interval and the minimum interval after a predetermined number of R waves have been counted;
   storing the detected difference between the maximum interval and the minimum interval between successive R waves after the predetermined number of R waves have occurred;
   measuring, during the course of surgery, the intervals between successive ones of the R waves;
   detecting the difference between the maximum interval and the minimum interval between successive ones of the R waves occurring during surgery while simultaneously counting the successive R waves;
   terminating measuring the intervals and detecting the difference between the maximum interval and the minimum interval between successive ones of the R waves after said predetermined number of R waves have been counted; and
   comparing the difference between the maximum interval and minimum interval between R waves determined prior to surgery with the difference between the maximum interval and minimum interval between R waves determined during surgery to determine the level of anaesthesia of the patient.

3. An apparatus for measuring the level of anaesthesia during surgery comprising:
   means for sensing the biopotentials including R waves of a patient's heart;
   an R wave discriminator receptive of the sensed biopotentials for discriminating the R waves;
   a counter cooperative with the R wave discriminator for counting the R waves;
   interval measuring means receptive of the R waves from said R wave discriminator for measuring the interval between consecutive R waves;
   detecting means cooperative with said interval measuring means for detecting the difference between the maximum interval and the minimum interval between consecutive R waves; and
   comparator means for comparing the detected difference between the maximum interval and the minimum interval between consecutive R waves with an initial value of the difference between the maximum interval and the minimum interval between consecutive R waves.

4. In an apparatus for measuring the level of anaesthesia according to claim 3, further comprising:
   a logical control circuit responsive to the number of R waves counted by said counter for disabling said interval measuring means and enabling said detecting means when the number of counted R waves exceeds a predetermined number; and
   wherein said comparator means includes a memory for storing said initial value of the difference between the maximum interval and the minimum interval between consecutive R waves, and a comparator for comparing the contents of said memory with the output of said detecting means.

* * * * *